United States Patent [19]

McCague

[11] Patent Number: 5,821,369
[45] Date of Patent: Oct. 13, 1998

[54] RACEMISATION PROCESS

[75] Inventor: Raymond McCague, Cambridgeshire, United Kingdom

[73] Assignee: Chiroscience Limited, United Kingdom

[21] Appl. No.: 797,524

[22] Filed: Feb. 7, 1997

[30] Foreign Application Priority Data

Feb. 8, 1996 [GB] United Kingdom .................. 9502516

[51] Int. Cl.$^6$ ........................ C07C 255/24; C07D 211/88
[52] U.S. Cl. ............................ 546/319; 558/354
[58] Field of Search ............... 558/354; 546/219

[56] References Cited

U.S. PATENT DOCUMENTS 2,848,455   8/1958   Hoffman et al. ..................... 546/219

FOREIGN PATENT DOCUMENTS 0 334633   9/1989   European Pat. Off. .
910014     6/1991   WIPO .
9205275    4/1992   WIPO .

*Primary Examiner*—Richard L. Raymond
*Attorney, Agent, or Firm*—Saliwanchik, Lloyd & Saliwanchik

[57] ABSTRACT

A process for the racemization of an enantiomerically-enriched compound of formula (3), comprises treatment of enantiomerically-enriched (3) with a base to obtain anion (4), optionally in protonated form, which is then combined with $CH_2=CH-Y^1$ to form racemic (3), $$X-(Ar)(Ak)C-(CH_2)_2-Y \quad (3)$$

$$X-(Ar)\overset{\ominus}{C}(Ak) \quad (4)$$

wherein Ar=aryl or heteroaryl; Ak=$C_{1-20}$ alkyl; X=CN, $CO_2R$, $CONR^1R^2$, and COR; Y and $Y^1$ are independently selected from CN, $CO_2R$, $CONR^1R^2$ and R, $R_1$ and $R_2$ are independently selected from H and $C_{1-20}$ alkyl; optionally as a salt thereof.

This racemization process can be used as part of an efficient synthesis of enantiomerically-enriched verapamil or aminoglutethimide.

17 Claims, No Drawings

RACEMISATION PROCESS

FIELD OF THE INVENTION

This invention relates to processes for the manufacture of single enantiomer forms of pharmaceutical drugs in which a structural characteristic is the presence of a chiral quanternary centre.

BACKGROUND OF THE INVENTION

Provision of high purity single enantiomer drugs for clinical use relies on the availability of efficient and reproducible means of production. Of the wide range of methodologies available to prepare such compounds, or precursors thereof, resolution of a racemate into constituent enantiomers, either by crystallisation of a suitable salt form (diastereomeric or conglomerate) or with a biocatalyst, is often the method of choice due to considerations of cost and scaleability.

The economics of a resolution approach are enhanced considerably if the unwanted enantiomer can be recycled for use in subsequent resolutions. In cases where the chiral centre of the racemisation substrate bears a hydrogen atom, racemisation is frequently a routine process, effected by treatment with basic or acidic reagents. In contrast, racemisation of compounds where the chiral centre is at a quaternary carbon presents a considerable challenge, since a simple deprotonation-reprotonation pathway is precluded. A number of pharmaceutical drugs have this feature, examples being verapamil (1, below) and aminoglutethimide (2, below), both marketed in racemic form, but with potential to utilise single enantiomers for enhanced therapeutic benefit.

Synthetic approaches to both (1) and (2) can proceed via structurally similar intermediates, represented by formula (3, below), in which Ar=aryl or heteroaryl; Ak=$C_{1-20}$ alkyl; X=CN, $CO_2R$, $CONNR^1R^2$, or COR; Y=CN, $CO_2R$, $CONR^1R^2$ or COR; and R, $R^1$ and $R^2$ are independently selected from H and $C_{1-20}$ alkyl. Efficient protocols for the resolution of (1) are described in a PCT Application claiming priority from British Application Nos. 9602515.0 and 9602514.3, and for the resolution of (2) in WO-A-9304058 and WO-A-9532947. However, no methods are documented for the recycling of compounds enriched in the unwanted enantiomer following resolution, and the present invention provides a generic solution to this problem.

SUMMARY OF THE INVENTION

According to the present invention, a process for the racemisation of an optically-enriched compound of formula (3), comprises treatment with a base to obtain anion (4), optionally in protonated form, which is then combined with $CH_2=CH-Y^1$, to form racemic (3),

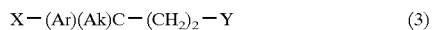

$$X-(Ar)(Ak)C-(CH_2)_2-Y \quad (3)$$

$$X-(Ar)C(Ak)^{\ominus} \quad (4)$$

wherein Ar=aryl or heteroaryl; Ak=$C_{1-20}$ alkyl; X=CN, $CO_2R$, $CONR^1R^2$, COR; Y and $Y^1$ are independently selected from CN, $CO_2R$, $CONR^1R^2$ and COR; and R, $R_1$ and $R_2$ are independently selected from H and $C_{1-20}$ alkyl.

The process is applicable to the manufacture of substantially single enantiomer aminoglutethimide and substantially verapamil single enantiomer, and analogues thereof.

DESCRIPTION OF THE INVENTION

The present invention is based upon the discovery that enantiomerically-enriched, or optically-enriched, compounds of formula (3) can be converted to the corresponding racemates with surprising efficiency by means of sequential retro-Michael fragmentation and Michael addition. When used in conjunction with a suitable resolution process, the present invention provides a means of maximising the yield of a desired enantiomer of (3) from a given quantity of the corresponding racemate.

The process of the present invention is depicted in Scheme 1, below. Treatment of an enantiomerically-enriched compound of formula (3) with a base effects a retro-Michael fragmentation resulting in anion (4), which then recombines with a Michael acceptor $CH_2=CH-Y^1$ to give compound (3) in racemic form. Typically, although not necessarily, the group $Y^1$ in the Michael acceptor is the same as Y in the starting material (3), more typically with the Michael acceptor having been derived from that starting material, i.e. as the other fragmentation product thereof. However, in some instances it may be beneficial to use a Michael acceptor with $Y^1$ different to Y, when incorporation of a different group into the molecule is desired. One example is the use of acrylonitrile as the Michael acceptor when Y is not CN.

A notable feature of the present invention is its generality, with applicability to compounds (3) wherein Ar can incorporate a range of substituents, both electron-withdrawing, for example nitro groups, and electron-donating, for example amino and alkoxy groups, such as methoxy.

Any base capable of promoting the desired fragmentation can be used in the process of the present invention. Suitable examples include metal alkoxides, metal hydrides, tertiary amines, and $(Me_2N)_3Si-M$, in which M=lithium, sodium or potassium, preferably metal alkoxide, eg. potassium tert-butoxide.

In a first embodiment of the present invention, a racemic compound (5, below), arising from retro-Michael fragmentation and protonation of the resultant anion (4, below), is isolated for use as a feedstock in a conjugate addition with a suitable Michael acceptor $CH_2=CH-Y^1$. The latter reaction is achieved under standard conditions, for example, as disclosed in DE-A-2059923 for synthesis of the verapamil intermediate (6, below).

In a second embodiment of the present invention, the overall process is carried out in a one-vessel operation. In this case, $Y^1=Y$, the process can be carried out in the presence of excess Michael acceptor $CH_2=CH-Y^1$, in order to replenish material consumed by polymerisation, reaction with the base, or evaporation. When $Y^1$ and Y are different, it is usually necessary to add the Michael acceptor in excess, in order to achieve the desired reaction product.

When it is desired to manufacture substantially single enantiomer aminoglutethimide or substantially single enantiomer verapamil a resolution procedure is first carried out on a racemic form of an appropriate compound (3), to give a desired and an undesired enantiomer, followed by racemisation of the undesired enantiomer using the process of the present invention, and then conversion of the desired enantiomer into the desired target compound.

If the target compound is aminoglutethimide, preferably compound (3) is one in which Ar is selected from phenyl, 4-aminophenyl and 4-nitrophenyl, preferably the latter, X=CN, and Y=$CO_2R$, preferably $CO_2Et$, more preferably with Ak=ethyl. After resolution and racemisation, racemic compound (3) can be converted to aminoglutethimide by, for instance, the method described in WO-A-9532947.

If the target compound is verapamil, preferably compound (3) is one in which Ar=3,4-dimethoxyphenyl, X=CN, and Y=CO$_2$R, more preferably with Ak=isopropyl. Again, after resolution and racemisation, racemic compound (3) can be converted to verapamil by conventional chemical techniques, for instance as described in DE-A-2059923, or more advantageously as described in British Patent Application no. 9618835.4.

In the context of the present Application, by enantiomerically-enriched we mean any non-racemic mixture of enantiomers. By substantially single enantiomer typically we mean that one enantiomer is present in an excess of at least 50% with regard to the other enantiomer, preferably at least 70%, and more preferably higher, for example at least 90%. If desired, enantiomeric excess can be increased by conventional recrystallisation techniques.

The invention is now illustrated by the following Examples.

EXAMPLE 1

Racemisation of ethyl 4-cyano-4-(4-nitrophenyl)hexanoate

A solution of potassium tert-butoxide (76 mg, 0.68 mmol) in anhydrous THF (2 ml) was added to ethyl 4-cyano-4-(4-nitrophenyl)hexanoate (38% ee, enriched in the (R)-enantiomer; 121 mg, 0.66 mmol). The resultant purple solution was stirred at ambient temperature for 40 hours, then diluted with water and extracted with ethyl acetate. The organic extract was dried and concentrated in vacuo to leave an oily residue, which was shown by NMR and chiral GC/MS analyses to contain ethyl 4-cyano-4-(4-nitrophenyl)hexanoate (7% ee, enriched in the (R)-enantiomer; 19%) and 2-(4-nitrophenyl)butanenitrile (56%).

EXAMPLE 2

Racemisation of methyl (S)-4-cyano-4-(3,4-dimethoxyphenyl)-5-methylhexanoate Potassium tert-butoxide (27.5 mg, 0.25 mmol) was added to a solution of methyl (S)-4-cyano-4-(3,4-dimethoxyphenyl)-5-methylhexanoate (150 mg, 0.491 mmol; 97% ee by chiral HPLC analysis) in anhydrous dimethyl sulphoxide (4 ml). The resulting golden yellow solution was stirred at room temperature for five minutes and then heated at 100° C. for 1 hour. The reaction mixture was then worked up by quenching with acetic acid and evaporation of solvent under high vacuum, followed by partitioning of the residue between methyl tert-butyl ether and water. The washed and dried organic extract was concentrated to provide methyl 4-cyano-4-(3,4-dimethoxyphenyl)-5-methylhexanoate as an oil (60 mg; 40% recovery). Chiral HPLC analysis of a sample removed prior to heating the reaction mixture at 100° C. showed methyl (S)-4-cyano-4-(3,4-dimethoxyphenyl)-5-methylhexanoate of substantially reduced enantiomeric purity (ca. 10% ee).

EXAMPLE 3

Racemisation of (S)-4-cyano-4-(3,4-dimethoxyhenyl)-5-methylhexanoic acid (R)-1-phenylethylamine salt Potassium tert-butoxide (171 mg, 1.5 mmol) was added to a solution of (S)-4-cyano-4-(3,4-dimethoxyhenyl)-5-methylhexanoic acid (R)-1-phenylethylamine salt (418 mg, 1.0 mmol; free acid of 99.1% ee by chiral HPLC analysis) in anhydrous dimethyl sulphoxide (5 ml). The resulting solution was stirred at room temperature for 30 minutes, and then heated 100° C. for 1 hour, and a further 3 hours at 130° C. The reaction mixture was then worked up by quenching with concentrated hydrochloric acid and evaporation of solvent under high vacuum, followed by partitioning of the residue between methyl tert-butyl ether and water. The dried organic extract was concentrated to leave 4-cyano-4-(3,4-dimethoxyhenyl)-5-methylhexanoic acid as an oil (216 mg; 73.5% recovery). Chiral HPLC analysis indicated that compared with starting material, the enantiomeric excess had reduced to 71%.

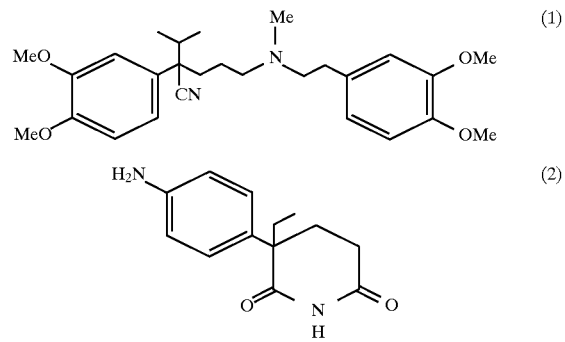

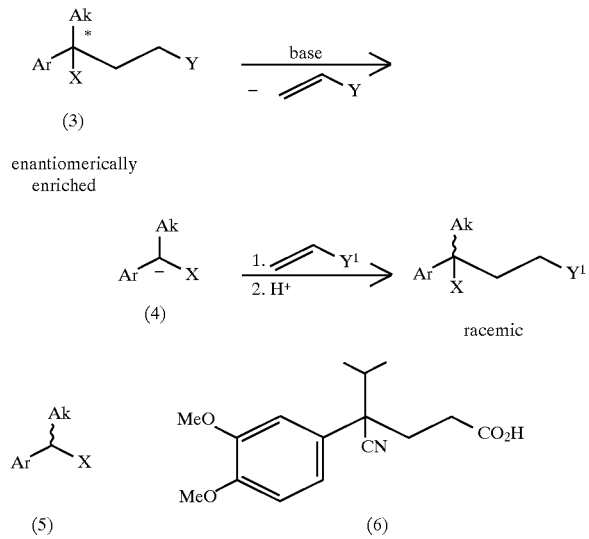

I claim:

1. A process for the racemisation of an enantiomerically-enriched compound of formula (3), which comprises treatment of enantiomerically-enriched (3) with a base capable of promoting a retro-Michael fragmentation to obtain anion (4), optionally in protonated form, which is then combined with CH$_2$=CH—Y$^1$ to form racemic X—(Ar)(Ak)C—(CH$_2$)$_2$—Y$^1$,

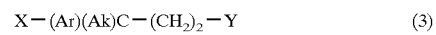

wherein Ar=aryl or heteroaryl; Ak=C$_{1-20}$ alkyl; X is selected from the group consisting of CN, CO$_2$R, CONR$^1$R$^2$, and COR; Y and Y$^1$ are independently selected from CN, CO$_2$R, CONR$^1$R$^2$, and COR; and R, R$^1$ and R$^2$ are independently selected from H and C$_{1-20}$ alkyl; optionally as a salt thereof.

2. The process, according to claim 1, wherein Y and Y$^1$ are the same.

3. The process, according to claim 2, wherein $CH_2=CH-Y^1$ is derived from enantiomerically-enriched compound (3).

4. The process, according to claim 1, wherein Y and $Y^1$ are different.

5. The process, according to claim 1, wherein Ar=phenyl or substituted phenyl, X=CN, and $Y=CO_2R$.

6. The process, according to claim 5, wherein Ar is selected from the group consisting of phenyl, 4-aminophenyl, and 4-nitrophenyl.

7. The process, according to claim 6, wherein Ar=4-nitrophenyl and $Y=Co_2Et$.

8. The process, according to claim 6, wherein Ak=ethyl.

9. The process, according to claim 5, wherein Ar=3,4-dimethoxyphenyl.

10. The process, according to claim 9, wherein Ak=isopropyl.

11. The process, according to claim 1, which is a one-pot process.

12. A process for preparing a substantially single enantiomer of aminoglutethimide, or an analogue thereof, comprising resolving a racemic compound of formula (3) in which Ar is selected from the group consisting of phenyl, 4-aminophenyl, and 4-nitrophenyl; X=CN; and Y=COOR ($R=C_{1-20}$ alkyl), to give a desired and an undesired enantiomer, racemising the undesired enantiomer using a process as defined in claim 6, and converting the desired enantiomer into aminoglutethimide, or the analogue thereof.

13. The process, according to claim 12, wherein the desired enantiomer is the (R)-enantiomer.

14. The process, according to claim 12, wherein the desired enantiomer is the (S)-enantiomer.

15. A process for preparing a substantially single enantiomer of verapamil, or an analogue thereof, comprising resolving a racemic compound of formula (3) in which Ar=3,4-dimethoxyphenyl and X=CN, to give a desired and an undesired enantiomer, racemising the undesired enantiomer using a process as defined in claim 9, and converting the desired enantiomer into verapamil, or the analogue thereof.

16. The process, according to claim 15, wherein the desired enantiomer is the (R)-enantiomer.

17. The process, according to claim 15, wherein the desired enantiomer is the (S)-enantiomer.

* * * * *